US009025854B2

United States Patent
Hayashi

(10) Patent No.: US 9,025,854 B2
(45) Date of Patent: May 5, 2015

(54) WAFER DEFECT INSPECTION APPARATUS AND METHOD FOR INSPECTING A WAFER DEFECT

(75) Inventor: Masashi Hayashi, Tokyo (JP)

(73) Assignee: SUMCO Corporation, Tokyo (JP)

( * ) Notice: Subject to any disclaimer, the term of this patent is extended or adjusted under 35 U.S.C. 154(b) by 271 days.

(21) Appl. No.: 13/103,159

(22) Filed: May 9, 2011

(65) Prior Publication Data
US 2011/0280470 A1    Nov. 17, 2011

(30) Foreign Application Priority Data

May 11, 2010  (JP) .................................. 2010-109520
May 11, 2010  (JP) .................................. 2010-109522

(51) Int. Cl.
| | |
|---|---|
| G06K 9/00 | (2006.01) |
| G01N 21/86 | (2006.01) |
| G01V 8/00 | (2006.01) |
| G01N 21/95 | (2006.01) |
| G06T 7/00 | (2006.01) |
| H01L 21/66 | (2006.01) |

(52) U.S. Cl.
CPC .......... *G01N 21/9505* (2013.01); *G06T 7/0004* (2013.01); *G06T 2207/10152* (2013.01); *G06T 2207/20148* (2013.01); *G06T 2207/30148* (2013.01); *H01L 22/12* (2013.01)

(58) Field of Classification Search
None
See application file for complete search history.

(56) References Cited

U.S. PATENT DOCUMENTS

| | | | |
|---|---|---|---|
| 6,630,996 B2 * | 10/2003 | Rao et al. ................... 356/237.5 |
| 7,632,349 B2 | 12/2009 | Itou et al. | |
| 7,729,528 B2 * | 6/2010 | O'Dell et al. .................. 382/149 |
| 8,055,058 B2 * | 11/2011 | Moon et al. .................... 382/145 |
| 2010/0085561 A1 | 4/2010 | Kamiyama et al. | |
| 2010/0165095 A1 | 7/2010 | Nakamura | |
| 2010/0309461 A1 | 12/2010 | Kamiyama et al. | |
| 2011/0025838 A1 | 2/2011 | Ninomiya | |

FOREIGN PATENT DOCUMENTS

JP    4358889    8/2009

\* cited by examiner

*Primary Examiner* — Thomas Conway
(74) *Attorney, Agent, or Firm* — Greenblum & Bernstein, P.L.C.

(57) ABSTRACT

It is an object to obtain an image of a wafer that is suitable for a defect inspection in an efficient manner.
It is judged whether or not an average gray level of an image of a wafer W that is an inspection target and that has been imaged by the light receiving part 2 is in the defect detectable range. A control processing part 6a is configured to modify an exposure time in imaging the wafer W and to obtain an image of the wafer W again by the light receiving part 2 in the case in which it is decided that an average gray level of an image of the wafer W is not in a defect detectable range, and an image processing part 6b is configured to carry out a defect inspection based on an image of the wafer W in the case in which it is decided that an average gray level of the image of the wafer W is in the defect detectable range.

8 Claims, 11 Drawing Sheets

| Defect type | Cross sectional gray level profile | Characteristic shape |
|---|---|---|
| Defect A |  |  |
| Defect B |  |  |
| Defect C |  |  |
| Defect D |  |  |
| Defect E |  |  |
| Defect F |  |  |

FIG. 4

| Classification name | | Gray level ratio 61a | | Gray level change rate 61b | | Area S 61 | | Circularity e 61d | | Long and short ratio 61e | | Acceptance judgment condition 62 | |
|---|---|---|---|---|---|---|---|---|---|---|---|---|---|
| | | Min | Max | Min | Max | Min | Max | Min | Max | Min | Max | Length 62a | Number 62b |
| Defect A | 凸 | 0 | 0.70 | 0 | 20 | 50 | — | 0.60 | 0.90 | — | — | — | 1 |
| Defect B | 凹 | 0.70 | 1.00 | 20 | — | 30 | — | 0.60 | 0.90 | 1.50 | 2.00 | — | 3 |
| Defect C | 凹 | 0.70 | 1.00 | 20 | — | 30 | — | 0.90 | 1.00 | 1.00 | 1.50 | — | 0 |
| Defect D | 凹 | 0.70 | 1.00 | 20 | — | 30 | 100 | — | — | — | — | 0.5 | 0 |
| Defect E | 凹 | 0.70 | 1.00 | 20 | — | 100 | — | — | 0.60 | 2.00 | — | — | 0 |
| Defect F | 凸 | 0.70 | 1.00 | — | — | 15 | — | — | 0.60 | 2.00 | — | — | 3 |
| Defect G (others) | 凹 | — | — | — | — | 10 | — | — | — | — | — | — | 0 |

Defect classification condition 6c

|  | Condition (1) | Condition (2) | Condition (3) | Condition (4) | Condition (5) | Condition (6) |
|---|---|---|---|---|---|---|
| Irradiation condition | Imax × 0.9 | Imax | Imax × 0.9 | Imax | | |
| Photodetective condition | Gmax × 0.5 | Gmax × 0.8 | Gmax | Gmax × 0.5 | Gmax × 0.8 | Gmax |
| Moving speed | High | | | Low | | |

WAFER DEFECT INSPECTION APPARATUS AND METHOD FOR INSPECTING A WAFER DEFECT

TECHNICAL FIELD

The present invention relates to a wafer defect inspection apparatus that is configured to inspect a defect of a wafer based on an image of the wafer that has been irradiated with an infrared light and to others.

BACKGROUND ART

A wafer defect inspection apparatus that is configured to inspect a defect that is on the surface or rear face of a wafer or inside a wafer has been known. For such a wafer defect inspection apparatus, one surface of the principal surfaces of a wafer is irradiated with an infrared light, the other surface of the principal surfaces of the wafer is imaged, and an image analysis processing is executed to the image for instance. By this configuration, a defect of a wafer is inspected.

For such a defect inspection of a wafer, the actual imaging is carried out while sampling a part of wafers for every lot in which a plurality of wafers is brought together for instance. By this configuration, an imaging condition (recipe) is decided for setting an average gray level of an image of a wafer in the range in which a defect can be detected in an appropriate manner (a defect detectable range). By using the recipe, a defect inspection is then carried out to all wafers in the lot.

As a technology related to an imaging in the case of a detection of a defect that is on the surface or rear face of a wafer or inside a wafer by using a transmitted light illumination, a technology has been known in which a value of a specific resistance of a wafer is obtained in advance, an intensity of illumination of an infrared light illuminating means is adjusted according to the value of a specific resistance, and a sensibility to an infrared light of an imaging means is adjusted (see Patent Literature 1).

CITATION LIST

Patent Literature

PTL 1
Japanese Patent No. 4358889

SUMMARY OF INVENTION

Technical Problem

As described above, a wafer is imaged in accordance with the same recipe for each of wafers in the same lot in a conventional method.

In recent years, a silicon wafer that is provided with a low resistivity (for instance, $P^{++}$ wafer (0.005 to 0.01 $\Omega \cdot cm$)) has been manufactured as a substrate wafer of an epitaxial silicon wafer. In the case in which the same recipe is applied to wafers in the same lot, an average gray level in a defect detectable range cannot be obtained for an image of a part of wafers unfortunately.

FIG. 1 is a view showing a relationship between an average gray level of each of wafers in a lot that is a measured target and a defect detectable range.

As shown in FIG. 1, a recipe that is applied to each lot is decided, and in the case in which a wafer is imaged while the recipe is applied to each of wafers in the lot, an average gray level of the image of the wafer becomes outside the defect detectable range in a lot of the $P^{++}$ wafer (a lot 1 of the $P^{++}$ wafer in FIG. 1) in some cases. Consequently, there is a possibility that a defect cannot be detected in an appropriate manner from an image of the imaged wafer.

On the other hand, in accordance with the technology that is described in Patent Literature 1, since it is necessary that a measuring apparatus configured to measure a specific resistance of a wafer is disposed and that a specific resistance is measured for a wafer, a time and an effort are required unfortunately.

Moreover, whether or not a defect of a wafer can be detected in an appropriate manner greatly depends on a method for processing an image of the imaged wafer.

The present invention was made in consideration of such conditions, and an object of the present invention is to provide a technique for obtaining an image of a wafer that is suitable for a defect inspection in an efficient manner.

Another object of the present invention is to provide a technique for detecting a defect from an image of a wafer in an appropriate manner.

Solution of Problem

A wafer defect inspection apparatus in accordance with a first aspect of the present invention comprises a wafer mounting means configured to mount a wafer that is an inspection target; an irradiation means configured to irradiate the wafer with an infrared light; an imaging means configured to image the wafer that has been irradiated with an infrared light; and an inspection means configured to inspect a defect of the wafer based on an image of the wafer that has been imaged by the imaging means. The wafer defect inspection apparatus further comprises a gray level judgment means configured to judge whether or not a reference gray level of an image of the wafer that is an inspection target and that has been imaged by the imaging means is in the predetermined gray level range; and a control means configured to modify an exposure time in imaging the wafer and to obtain an image of the wafer again by the imaging means in the case in which it is decided that a reference gray level of an image of the wafer is not in the predetermined gray level range, wherein the inspection means is configured to carry out a defect inspection based on an image of the wafer in the case in which it is decided that a reference gray level of the image of the wafer is in the predetermined gray level range.

According to the above wafer defect inspection apparatus, an image in which a reference gray level of an image of the wafer is in the predetermined gray level range can be obtained by modifying an exposure time in imaging the wafer. Consequently, a defect of a wafer can be inspected in an appropriate manner.

For the above wafer defect inspection apparatus, the irradiation means is configured to irradiate the wafer with the infrared light in a line pattern, the imaging means is an image line sensor, and the control means is configured to obtain an image of the entire wafer by relatively moving the irradiation means, the imaging means, and the wafer mounting means. According to the above wafer defect inspection apparatus, an image of the entire wafer can be obtained in an appropriate manner.

For the above wafer defect inspection apparatus, the irradiation means and the imaging means are disposed on the opposite sides from each other across the wafer mounted on the wafer mounting means. According to the above wafer defect inspection apparatus, an image of the wafer that has been irradiated with an infrared light can be obtained by using a transmitted light.

For the above wafer defect inspection apparatus, the control means is configured to modify a relative velocity of the irradiation means and the imaging means to the wafer mounting means and to modify the exposure time by changing an image capture rate of the imaging means in the case in which it is decided that a reference gray level of an image of the wafer is not in the predetermined gray level range. According to the above wafer defect inspection apparatus, a gray level of each of the picture elements for an image of the wafer can be modified in an appropriate manner.

For the above wafer defect inspection apparatus, the control means is configured to adjust at least one of the intensity of the infrared light of the irradiation means or a photodetective sensitivity of the imaging means and to obtain an image of the wafer again in the case in which it is decided that a reference gray level of an image of the wafer is not in the predetermined gray level range, and is configured to adjust the exposure time in the case in which the gray level is not in the predetermined gray level range even if the intensity of the infrared light and the photodetective sensitivity of the imaging means are adjusted. According to the above wafer defect inspection apparatus, since the exposure time is adjusted in the case in which the gray level is not in the predetermined gray level range even if the intensity of the infrared light and the photodetective sensitivity of the imaging means are adjusted, a frequency of an adjustment using the exposure time can be reduced.

A method for inspecting a wafer defect in accordance with a second aspect of the present invention comprises the steps of irradiating a wafer that is an inspection target with an infrared light, imaging the wafer that has been irradiated with an infrared light, and inspecting a defect of the wafer based on an image of the wafer. The method for inspecting a wafer defect comprises the step of irradiating a wafer with an infrared light and imaging the wafer; the step of judging whether or not a reference gray level of an image of the wafer that is an inspection target and that has been imaged is in the predetermined gray level range; the step of modifying the exposure time in imaging the wafer and obtaining an image of the wafer again in the case in which it is decided that a reference gray level of an image of the wafer is not in the predetermined gray level range; and the step of carrying out a defect inspection of the wafer based on an image of the wafer in the case in which it is decided that a reference gray level of the image of the wafer is in the predetermined gray level range.

According to the above method for inspecting a wafer defect, an image in which a reference gray level of an image of the wafer is in the predetermined gray level range can be obtained by modifying an exposure time in imaging the wafer. Consequently, a defect of a wafer can be inspected in an appropriate manner.

A wafer defect inspection apparatus in accordance with a third aspect of the present invention comprises a wafer mounting means configured to mount a wafer that is an inspection target; an irradiation means configured to irradiate the wafer with an infrared light; an imaging means configured to image the wafer that has been irradiated with an infrared light; and an inspection means configured to inspect a defect of the wafer based on an image of the wafer that has been imaged by the imaging means. The wafer defect inspection apparatus further comprises a reference average gray level calculation means configured to calculate a gray level that has been obtained by averaging gray level of a plurality of picture elements in the predetermined range including the picture element in a plurality of picture elements that are arranged in the predetermined line direction as a reference average gray level of each picture element for the picture elements in a range that is an inspection target of the wafer in the image; a differential value calculation means configured to calculate a differential value between the reference average gray level of each of the picture elements and a gray level of each of the picture elements; a defect candidate picture element judgment means configured to judge whether each of the picture elements is a defect candidate picture element or not by comparing the differential value for each of the picture elements with the predetermined threshold value; and an inspection means configured to inspect a defect of the wafer based on the defect candidate picture element. According to the above wafer defect inspection apparatus, since whether or not each of the picture elements is a defect candidate picture element is judged by comparing a differential value between the reference average gray level of each of the picture elements and a gray level of each of the picture elements with the threshold value, the non-uniformity of an image and the influence of a difference of a level of a gray level for every wafer can be reduced. Consequently, a defect candidate picture element can be detected in a more appropriate manner.

The above wafer defect inspection apparatus further comprises a threshold value decision means configured to decide the predetermined threshold value to each of the picture elements based on the reference average gray level of each of the picture elements. According to the above wafer defect inspection apparatus, since a threshold value is decided based on the reference average gray level, the appropriate threshold value can be decided for every image and a defect can be detected in an appropriate manner.

For the above wafer defect inspection apparatus, the threshold value decision means is configured to decide a value that is obtained by multiplying the reference average gray level by the predetermined value as the predetermined threshold value. According to the above wafer defect inspection apparatus, a threshold value can be easily decided from the reference average gray level in an appropriate manner.

For the above wafer defect inspection apparatus, the reference average gray level calculation means is configured to calculate the reference average gray level while supposing that a gray level of a picture element in a region that is exempt from the inspection is a gray level of a picture element of a boundary with the region that is an inspection target in the case in which a picture element in the predetermined range in the predetermined line direction is corresponded to the picture element in the region that is exempt from the inspection around the outer circumference of the wafer. According to the above wafer defect inspection apparatus, an influence for the reference average gray level due to a gray level of a picture element in a range that is exempt from the inspection can be reduced and a defect candidate picture element can be detected in a more appropriate manner.

For the above wafer defect inspection apparatus, the reference average gray level calculation means is configured to calculate the reference average gray level while supposing that a gray level of a picture element in a region that is exempt from the inspection is a gray level of a picture element at a symmetric position to a boundary with the region that is an inspection target on the straight line in the predetermined line direction in the case in which a picture element in the predetermined range in the predetermined line direction is corresponded to the picture element in the region that is exempt from the inspection around the outer circumference of the wafer. According to the above wafer defect inspection apparatus, an influence for the reference average gray level due to a gray level of a picture element in a range that is exempt from the inspection can be reduced and a defect candidate picture element can be detected in a more appropriate manner.

For the above wafer defect inspection apparatus, the inspection means comprises a defect candidate region specification means configured to specify a defect candidate region based on the defect candidate picture element; and a defect type judgment means configured to judge whether a defect candidate region is corresponded to the predetermined defect type or not based on at least one of the concave/convex of a gray level profile of the defect candidate region, a gray level ratio that is a ratio between the maximum difference of a gray level and a reference average gray level for the defect candidate region and a reference average gray level, a rate of change of a gray level which is the maximum gray level change (an absolute value of an inclination of a gray level profile) in a range that has been specified for a defect candidate region boundary, an area of the defect candidate region, a circularity of the defect candidate region, and a ratio between a long width and a short width in the case in which a center of gravity of the defect candidate region is supposed as a reference. According to the above wafer defect inspection apparatus, a defect candidate region that is corresponded to the predetermined defect type can be decided in an appropriate manner.

For the above wafer defect inspection apparatus, the inspection means further comprises an acceptance judgment means configured to judge whether the wafer is acceptable or not as a product based on the number of defect candidate regions that are corresponded to the predetermined defect type. According to the above wafer defect inspection apparatus, it is possible to judge whether the wafer is acceptable or not as a product in an appropriate manner.

A method for inspecting a wafer defect in accordance with a fourth aspect of the present invention is a method for inspecting a wafer defect based on an image of a wafer that is an inspection target and comprises the step of calculating a gray level that has been obtained by averaging gray level of a plurality of picture elements in the predetermined range including the picture element in a plurality of picture elements that are arranged in the predetermined line direction as a reference average gray level of each picture element for the picture elements in a range that is an inspection target of the wafer in the image; the step of calculating a differential value between the reference average gray level of each of the picture elements and a gray level of each of the picture elements; the step of judging whether each of the picture elements is a defect candidate picture element or not by comparing the differential value for each of the picture elements with the predetermined threshold value; and the step of inspecting a defect of the wafer based on the defect candidate picture element. According to the above wafer defect inspection apparatus, since whether or not each of the picture elements is a defect candidate picture element is judged by comparing a differential value between the reference average gray level of each of the picture elements and a gray level of each of the picture elements with the threshold value, the non-uniformity of an image and the influence of a difference of a grayscale level of a gray level for every wafer can be reduced. Consequently, a defect candidate picture element can be detected in a more appropriate manner.

BRIEF DESCRIPTION OF THE DRAWINGS

FIG. 4 is a view showing a defect judgment table in accordance with an embodiment of the present invention.

MODE FOR CARRYING OUT THE INVENTION

An embodiment of the present invention will be described below in detail with reference to the drawings. The preferred embodiments that will be described in the following do not limit the present invention in accordance with the claims, and all of the elements and combinations thereof that will be described in the embodiments are not essential for solution means of the present invention.

A wafer defect inspection apparatus in accordance with an embodiment of the present invention will be described in detail in the following.

Figure 1:
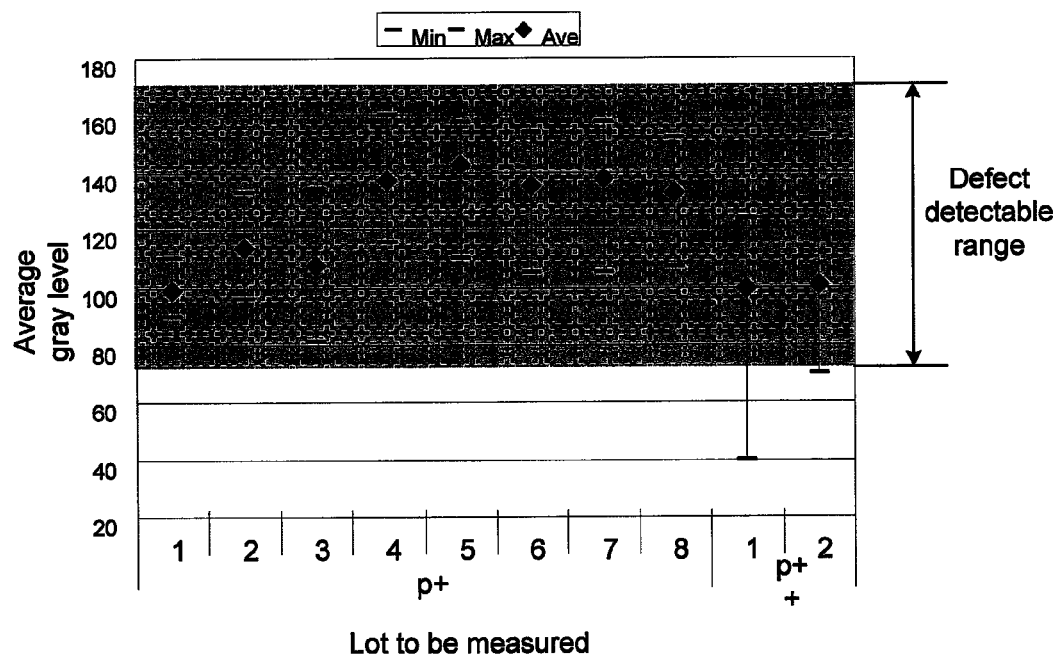
FIG. 1 is a view showing a relationship between an average gray level of each of wafers in a lot that is a measured target and a defect detectable range.
Figure 2A:
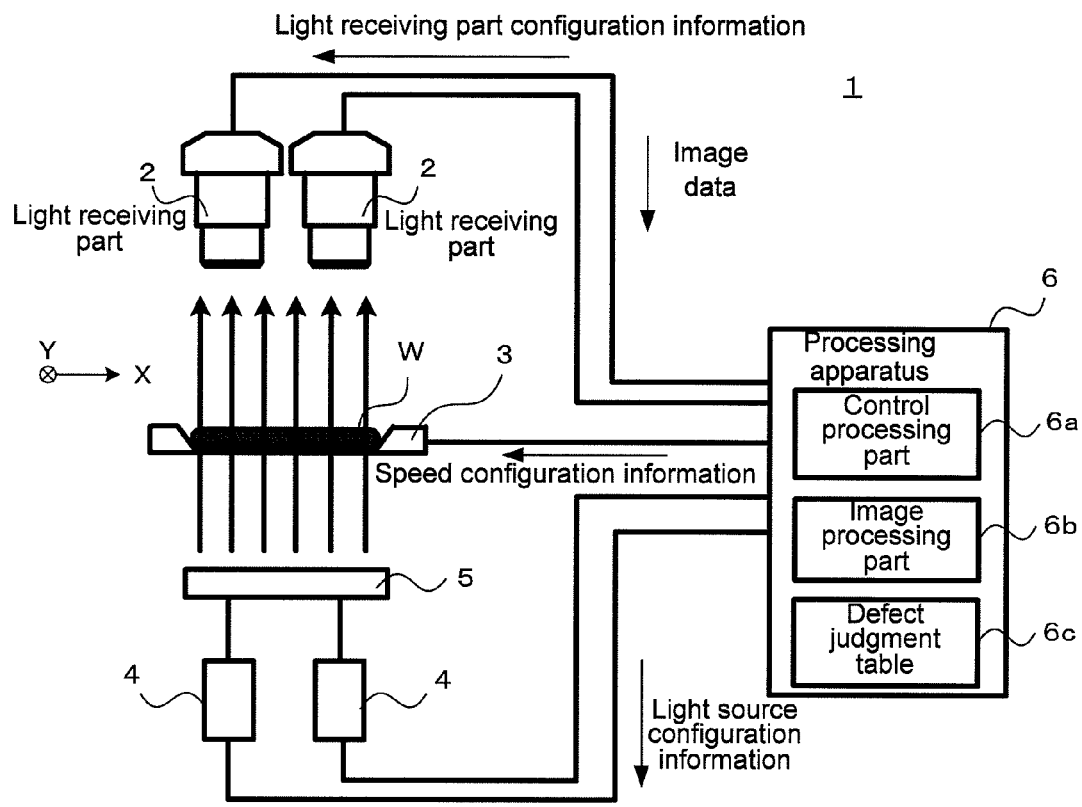
FIG. 2 is a block diagram of a wafer defect inspection apparatus in accordance with an embodiment of the present invention.
Figure 2B:
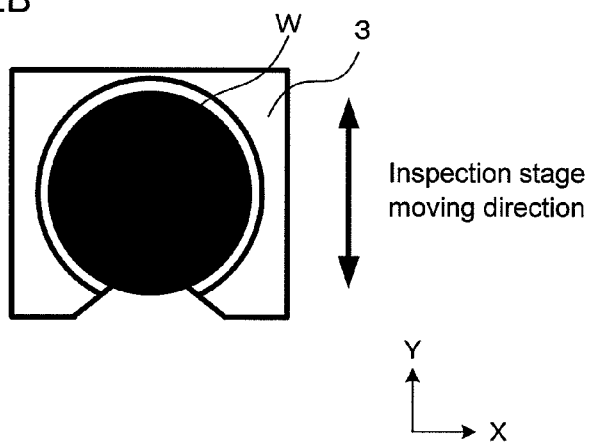

FIG. 2 is a block diagram of a wafer defect inspection apparatus in accordance with an embodiment of the present invention. FIG. 2A is a block diagram of a wafer defect inspection apparatus that is viewed from a side face, and FIG. 2B is a block diagram of an inspection stage of a wafer defect inspection apparatus that is viewed from up above.

A wafer defect inspection apparatus 1 is provided with an inspection stage 3 that is an example of a wafer mounting means that is configured to mount a wafer W that is an inspection target, at least one illuminating part 4 that is configured to irradiate the wafer with an infrared light, a light guide 5 that is configured to shape an infrared light that has been irradiated from the illuminating part 4 to be a light in a line pattern that is provided with the light intensity almost equivalent to that of the infrared light and to project the light to the wafer W, at least one light receiving part 2 that is an example of an imaging means that is configured to capture an image of the wafer W, and a processing apparatus 6. The illuminating part 4 and the light guide 5 configure an illuminating means.

The light receiving part 2 is provided with an image line sensor having the sensitivity to an infrared light, and is placed in such a manner that a light receiving face of the image line sensor is facing the inspection stage 3, that is, facing downward. For the present embodiment, each of the light receiving parts 2 is used for capturing an image of a half of the wafer W (the light receiving part 2 on the left side in FIG. 2A captures an image of the left half face of the wafer W and the light receiving part 2 on the right side in FIG. 2A captures an image of the right half face of the wafer W).

For the wafer defect inspection apparatus 1, the light guide 5 and the image line sensor of each of the light receiving parts 2 are disposed on the opposite sides from each other across the inspection stage 3. In other words, a light in a line pattern that is projected by the light guide 5 travels along the line of the image line sensor of the light receiving part 2.

The inspection stage 3 can move linearly in the Y direction (a perpendicular direction of the plane of the paper of FIG. 2A, a vertical direction in FIG. 2B).

The processing apparatus 6 is provided with a control processing part 6a that is an example of a gray level judgment means and a control means, an image processing part 6b that is an example of a reference average gray level calculation means, a differential value calculation means, a defect candidate picture element judgment means, a threshold value decision means, an inspection means, a defect candidate region specification means, a defect type judgment means, and an acceptance judgment means, and a defect judgment table 6c.

The control processing part 6a is configured to control the sensitivity (gain) to the intensity of a light for the image line sensor of the light receiving part 2. Moreover, the control processing part 6a is configured to control an image capture rate for the image line sensor of the light receiving part 2. In the present embodiment, the control processing part 6a controls the light receiving part 2 by transmitting the light receiving part configuration information including a photodetective condition (the sensitivity) and a part of the exposure conditions (an image capture rate) to the light receiving part 2. Moreover, the control processing part 6a receives the image data of the wafer W that has been imaged by the light receiving part 2 (the gray level data of each of the picture elements) and sends the data to the image processing part 6b. Furthermore, the control processing part 6a controls the intensity of the infrared light that is irradiated by the illuminating part 4. In the present embodiment, the control processing part 6a controls the illuminating part 4 by transmitting the light source configuration information including an irradiation condition (the intensity of a light) to the illuminating part 4. Moreover, the control processing part 6a controls a moving speed of the inspection stage 3. In the present embodiment, the control processing part 6a controls a moving speed of the inspection stage 3 by transmitting the speed configuration information including a part of the exposure conditions (a specification of a moving speed) to a driving part (not shown) of the inspection stage 3.

The image processing part 6b executes a defect detection image analysis processing in which a defect of the wafer W is inspected based on the image data that has been sent from the control processing part 6a. The image processing part 6b executes the processing by using the defect judgment table 6c (see Table 4) that stores a condition for specifying a type of a defect (a defect classification condition) and a condition for deciding an acceptance/rejection of a wafer (whether the wafer is acceptable or not as a product) (an acceptance judgment condition) in the defect detection image analysis processing. The processing of the image processing part 6b will be described later in detail.

Figure 3:
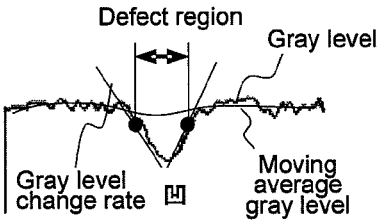
FIG. 3 is a view showing an example of a gray level profile that is detected by a defect inspection in accordance with an embodiment of the present invention.
Figure 3:
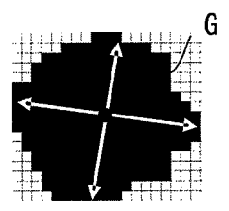
Figure 3:
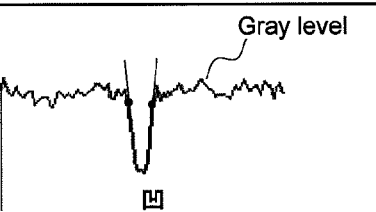
Figure 3:
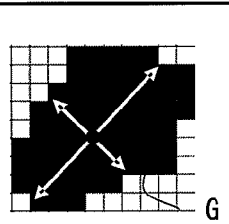
Figure 3:
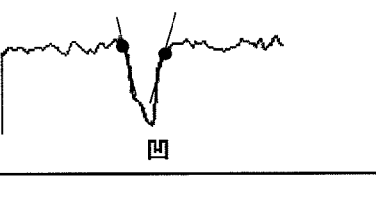
Figure 3:
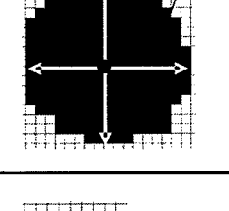
Figure 3:
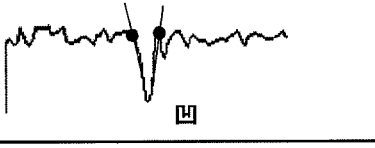
Figure 3:
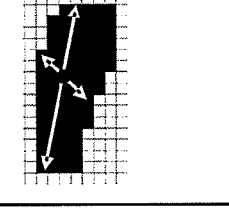
Figure 3:
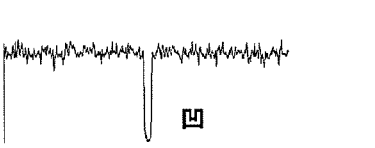
Figure 3:
Figure 3:
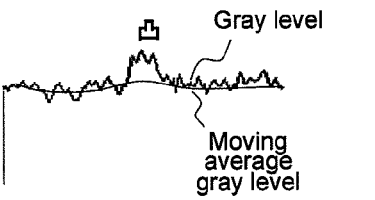
Figure 3:
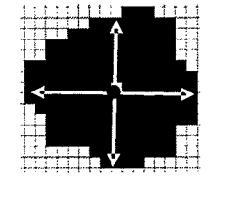

FIG. 3 is a view showing an example of a gray level profile that is detected by a defect inspection in accordance with an embodiment of the present invention.

As a type of a defect of the wafer W, there can be mentioned for instance a defect having a wide variety of different generation modes such as a void (air bubble), a film pinhole, a contamination, a stain spot, a foreign matter, a flaw, and a crack. Consequently, as shown in FIG. 3, a gray level of a defect region is below a moving average gray level that is described later, whereby a shape of a profile of a gray level is detected in a concave pattern (defects A to E), or a gray level of a defect region is above a moving average gray level, whereby a shape of a profile of a gray level is detected in a convex pattern (defect F) for instance depending on a type of a defect. In other words, a gray level profile that is detected is different depending on a type of a defect. In the case in which a shape of a gray level profile that has been detected is in a similar concave pattern (for instance, defects A to E), a type of a defect cannot be distinctly decided by only a gray level profile in some cases. However, a type of a defect can be decided by a circularity described later or a ratio between the longest straight line (the maximum width) and the shortest straight line (the minimum width) that pass through a gravity center G of the defect region.

FIG. 4 is a view showing a defect judgment table in accordance with an embodiment of the present invention.

The defect judgment table 6c can store a plurality of records that are provided with a classification name field 60, a defect classification condition field 61, and an acceptance judgment condition field 62. Each of the configurations for the defect judgment table 6c can be decided in a fixed manner, or a user can decide the configurations in an appropriate manner by using an input apparatus (not shown).

The classification name field 60 stores a classification name of a defect.

The defect classification condition field 61 stores a condition in classifying a defect for a defect candidate region that is described later (a defect classification condition). In the present embodiment, the defect classification condition field 61 is provided with a concave/convex field 61a, a gray level ratio field 61b, a gray level change rate field 61c, an area field 61d, a circularity field 61e, and a long and short ratio field 61f. In the defect classification condition field 61 of the present embodiment, at least one condition of the conditions that are indicated by the fields 61a to 61f is set. In a condition that is used for the classification, a value for the condition is set. On the other hand, in a condition that is not used for the classification, a non-setting symbol that indicates a non-setting is shown ("-" is shown in the present embodiment).

In the concave/convex field 61a, a concave or a convex of a gray level profile, which is a condition for judging a defect of a corresponded classification, is set for a defect candidate region. More specifically, a condition is set for judging whether a gray level profile of the region is in a concave pattern (a low state) or in a convex pattern (a high state) to a moving average gray level of the region. In the gray level ratio field 61b, the minimum value (Min) and/or the maximum value (Max) of a gray level ratio that is a condition for judging a defect of a corresponded classification are set for a ratio (a gray level ratio) of a moving average gray level and the maximum value of a difference between a gray level in a defect candidate region and a moving average gray level. In the gray level change rate field 61c, the minimum value (Min) and/or the maximum value (Max) of a gray level change rate that is a condition for judging a defect of a corresponded classification are set. The gray level change rate indicates the maximum value of a change of a gray level (an absolute value of an inclination of a gray level profile) in a range that has been specified in advance for a defect candidate region boundary that passes through a gravity center G. In the area field 61d, the minimum value (Min) and/or the maximum value (Max) of an area S that is a condition for judging a defect of a corresponded classification are set. In the circularity field 61e, the minimum value (Min) and/or the maximum value (Max) of a circularity that is a condition for judging a defect of a corresponded classification are set. In the long and short ratio field 61f, the minimum value (Min) and/or the maximum value (Max) of the long and short ratio that is a condition for judging a defect of a corresponded classification are set. The long and short ratio indicates a ratio between the longest straight line (the maximum width) and the shortest straight line (the minimum width) that pass through a gravity center G for the target region.

The acceptance judgment condition field 62 is provided with a length field 62a and a number field 62b.

The length field 62a stores a length that is permissible as a product of a wafer to a defect region that is classified as a corresponded defect classification, which is a condition that is used for an acceptance judgment. More specifically, it is indicated that a wafer is acceptable as a product in the case in which a length of a defect that has been decided as a corresponded defect classification is within a permissible length, and a wafer is unacceptable as a product in the case in which a length of a defect exceeds a permissible length. The number field 62b stores a number (a permissible number) that is permissible as a defect region that is classified as a corresponded defect classification, which is a condition that is used for an acceptance judgment. More specifically, it is indicated that a wafer is unacceptable as a product in the case in which the number of defects that have been decided as a corresponded defect classification exceeds a permissible number. In the fields 62a and 62b, a numerical value is set for a condition that is used for an acceptance judgment, and a non-setting symbol that indicates a non-setting is shown in a condition that is not used for an acceptance judgment ("-" is shown in the present embodiment).

For a condition that is classified as a defect B that is a second record in FIG. 4 for instance, it is indicated that the wafer is acceptable as a product in the case in which a gray level profile is in a concave pattern, a gray level ratio is in the range of 0.70 to 1.00, an area S is at least 30 (picture elements), a circularity e is in the range of 0.60 to 0.90, the long and short ratio is in the range of 1.50 to 2.00, and there are up to three defect regions that are classified as the defect B.

Figure 5:
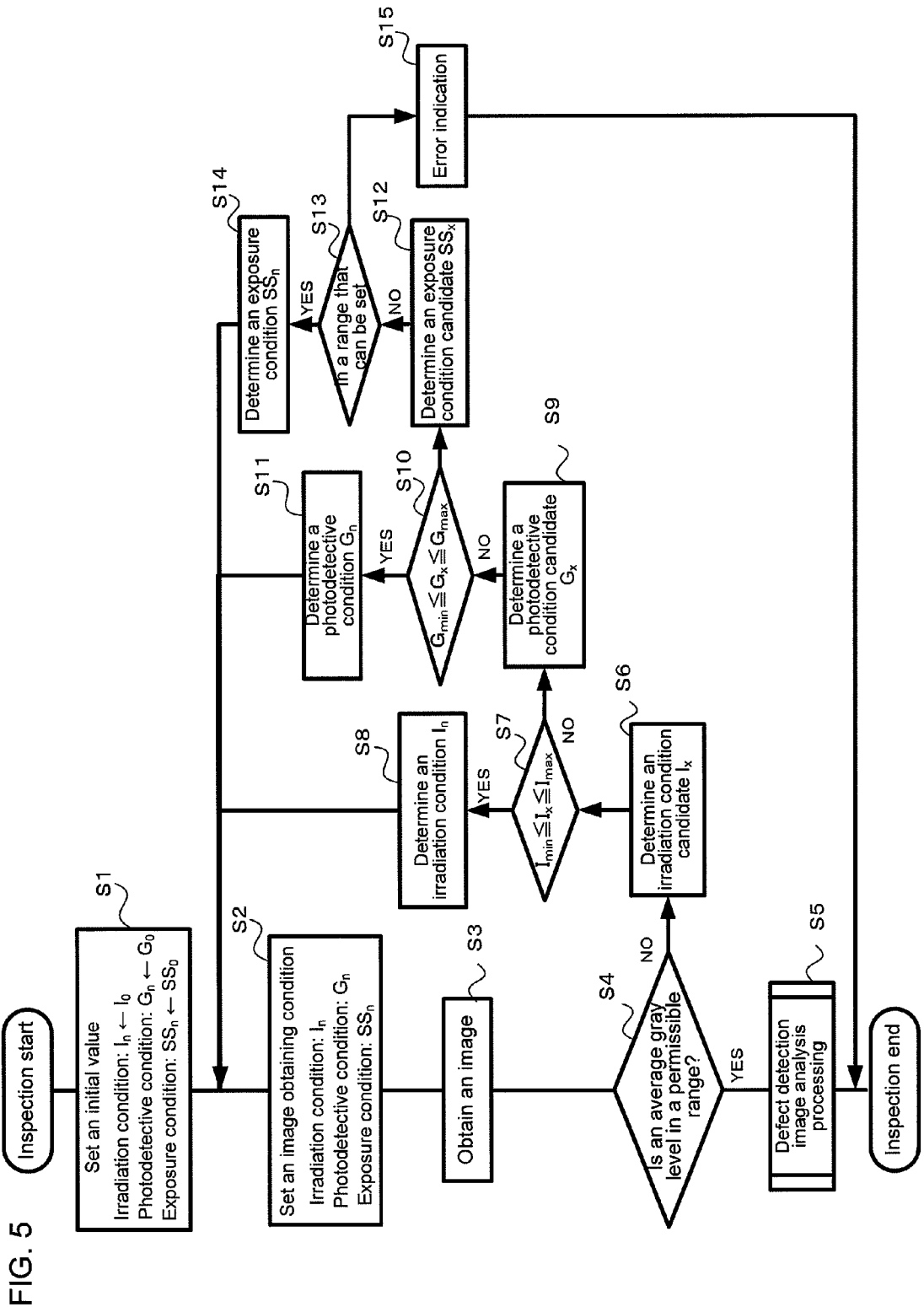
FIG. 5 is a flowchart of a defect inspection processing in accordance with an embodiment of the present invention.

FIG. 5 is a flowchart of a defect inspection processing in accordance with an embodiment of the present invention.

In the first place, the control processing part 6a sets an initial value to a setting condition in obtaining an image of the wafer W (an image obtaining condition) (step S1). More specifically, the control processing part 6a sets an initial value $I_0$ to an irradiation condition $I_n$ for the illuminating part 4, an initial value $G_0$ to a photodetective condition $G_n$ for the light receiving part 2, and an initial value $SS_0$ to an exposure condition $SS_n$ that is corresponded to an exposure time (an image capture rate of the light receiving part 2 and a moving speed of the inspection stage 3). In the present embodiment, the initial value $I_0$ is the light intensity value smallest in the range of an intensity of a light that is used in obtaining an image. The initial value $G_0$ is the gain value smallest in the range of a gain that is used in obtaining an image. The initial value $SS_0$ is a value that is corresponded to the exposure time shortest in exposure conditions that are used in obtaining an image. (In the present embodiment, the initial value $SS_0$ is the moving speed highest in the range of a moving speed that is used in obtaining an image, and is the image capture rate highest in the range of an image capture rate that is used in obtaining an image.)

In the next place, the control processing part 6a sets a setting condition in obtaining an image of the wafer W to the light receiving part 2, the inspection stage 3, and the illuminating part 4 (step S2), and obtains an image of the entire wafer W from the light receiving part 2 by operating the light receiving part 2, the inspection stage 3, and the illuminating part 4 (step S3).

In the next place, the control processing part 6a judges whether or not an average gray level of an image that has been obtained is in a permissible gray level range (a permissible range: a defect detectable range) (step S4). For instance, the control processing part 6a carries out a judgment depending on whether $|A_n - A_t| \leq \delta A_t$ is satisfied or not, where $A_n$ is an average gray level of an image of the wafer W, $A_t$ is a central gray level of a permissible range, and $\delta A_t$ is a permissible shift intensity from the central gray level of a permissible range. The permissible range can be represented as $A_t \pm \delta A_t$. The permissible range can be in the range of 70 to 170 in the case in which a value of a gray level is in the range of 0 to 255 for instance.

As a result, in the case in which it is decided that an average gray level is in a permissible range (step S4: YES), it is indicated that the image is provided with a gray level that is suitable for a defect detection. Consequently, the control processing part 6a sends an image data to the image processing part 6b and makes the image processing part 6b to execute a defect detection image analysis processing (step S5).

On the other hand, in the case in which it is decided that an average gray level is not in a permissible range (step S4: NO), it is indicated that the image is not provided with a gray level that is suitable for a defect detection. Consequently, the control processing part 6a determines an irradiation condition candidate $I_x$ for obtaining an image that is provided with a gray level that is more suitable (step S6). In the present embodiment, the control processing part 6a obtains the irradiation condition candidate $I_x$ by calculating $I_x = k^* A_t / A_n^* I_n$, where k is a predetermined coefficient.

In the next place, the control processing part 6a judges whether or not the irradiation condition candidate $I_x$ is in a range that can be set, that is, the irradiation condition candidate $I_x$ satisfies $I_{min} \leq I_x \leq I_{max}$ ($I_{min}$: the settable minimum value of I, $I_{max}$: the settable maximum value of I) (step S7). In the case in which it is decided that the irradiation condition candidate $I_x$ is in a range that can be set (step S7: YES), the irradiation condition candidate $I_x$ is determined as an irradiation condition $I_n$ (step S8) and the step S2 is then executed. By this configuration, an irradiation condition (an intensity of a light of the illuminating part 4) can be modified in such a manner that an average gray level of an image of the wafer W comes close to the permissible range.

On the other hand, in the case in which it is decided that the irradiation condition candidate $I_x$ is not in a range that can be set (step S7: NO), the control processing part 6a determines a photodetective condition candidate $G_x$ for obtaining an image that is provided with a gray level that is more suitable (step S9). In the present embodiment, the control processing part 6a obtains the photodetective condition candidate $G_x$ by calculating $G_x = l^* A_t / A_n^* G_n$, where l is a predetermined coefficient.

In the next place, the control processing part 6a judges whether or not the photodetective condition candidate $G_x$ is in a range that can be set, that is, the photodetective condition candidate $G_x$ satisfies $G_{min} \leq G_x \leq G_{max}$ ($G_{min}$: the settable minimum value of G, $G_{max}$: the settable maximum value of G) (step S10). In the case in which it is decided that the photodetective condition candidate $G_x$ is in a range that can be set (step S10: YES), the photodetective condition candidate $G_x$ is determined as a photodetective condition $G_n$ (step S11) and the step S2 is then executed. By this configuration, a photodetective condition (a gain of the light receiving part 2) can be modified in such a manner that an average gray level of an image of the wafer W comes close to the permissible range.

On the other hand, in the case in which it is decided that the photodetective condition candidate $G_x$ is not in a range that can be set (step S10: NO), the control processing part 6a determines an exposure condition candidate $SS_x$ for obtaining an image that is provided with a gray level that is more suitable (step S12). In the present embodiment, the control processing part 6a determines the condition in which an exposure time is longer than $SS_n$ as the exposure condition candidate $SS_x$ (the condition in which a moving speed of the inspection stage 3 is made lower and an image capture rate of the light receiving part 2 is made lower).

In the next place, the control processing part 6a judges whether or not the exposure condition candidate $SS_x$ is in a range that can be set (step S13). In the case in which it is decided that the exposure condition candidate $SS_x$ is in a range that can be set (step S13: YES), the exposure condition candidate $SS_x$ is determined as an exposure condition $SS_n$ (step S14) and the step S2 is then executed. By this configuration, an exposure condition (a moving speed of the inspection stage 3 and an image capture rate of the light receiving part 2) can be modified in such a manner that an average gray level of an image of the wafer W comes close to the permissible range.

On the other hand, in the case in which it is decided that the exposure condition candidate $SS_x$ is not in a range that can be set (step S13: NO), an exposure condition cannot be modified, which means that a condition for obtaining an image that is provided with a suitable gray level cannot be set. Consequently, the control processing part 6a executes an error indication on a display apparatus not shown (step S15).

By the above configuration, an image obtaining condition in obtaining an image of the wafer W can be adjusted and an image that is provided with a gray level suitable for the defect detection for the wafer W can be obtained in an appropriate manner.

Figures 6A, 6B:
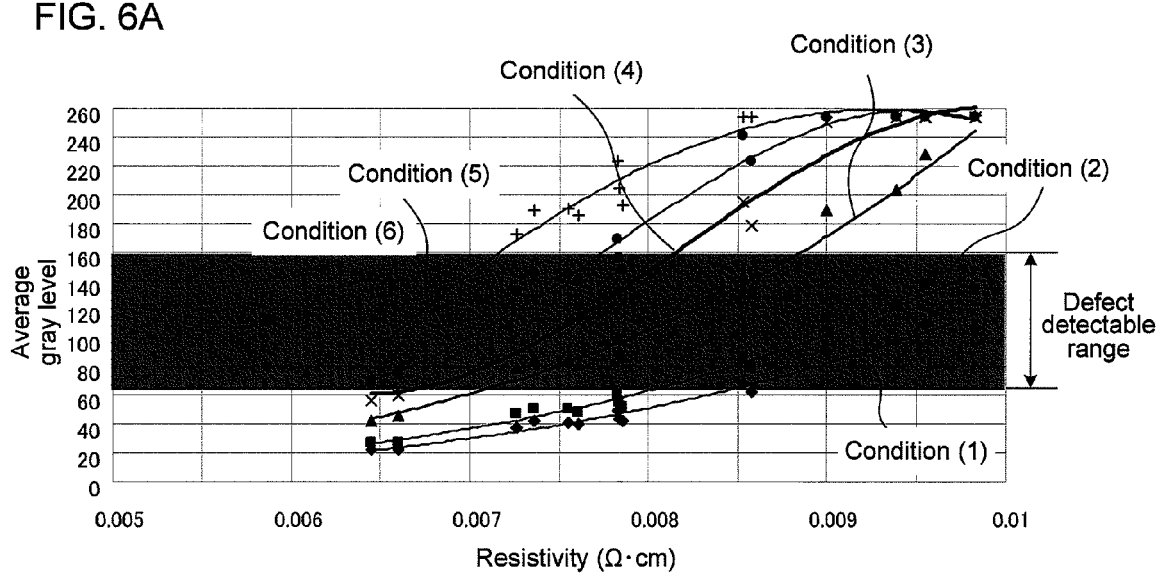
FIG. 6 is a view illustrating a relationship between the resistivity of a wafer and an average gray level of an image of a wafer to a plurality of image obtaining conditions in accordance with an embodiment of the present invention.

FIG. 6 is a view illustrating a relationship between the resistivity of a wafer and an average gray level of an image of a wafer to a plurality of image obtaining conditions in accordance with an embodiment of the present invention. FIG. 6A is a view illustrating a relationship between the resistivity of a wafer W and an average gray level of the wafer W to a plurality of image obtaining conditions. FIG. 6B is a view illustrating the image obtaining conditions (1) to (6).

As shown in the case in which a condition (1) is changed to a condition (2) for instance, only a gain of the light receiving part 2 is increased. In this case, as shown in the graph that is corresponded to the condition (1) and the condition (2) of FIG. 6A, an average gray level of an image of the wafer W that is provided with a lower resistivity can be included in a defect detectable range. In other words, an image of the wafer W that is provided with a lower resistivity can be captured in an appropriate manner.

As shown in the case in which a condition (2) is changed to a condition (3) for instance, a gain of the light receiving part 2 is increased and an intensity of a light of the illuminating part 4 is increased. In this case, as shown in the graph that is corresponded to the condition (2) and the condition (3) of FIG. 6A, an average gray level of an image of the wafer W that is provided with a lower resistivity can be included in a defect detectable range. In other words, an image of the wafer W that is provided with a lower resistivity can be captured in an appropriate manner.

As shown in the case in which a condition (2) is changed to a condition (4) for instance, a moving speed of the inspection stage 3 is made lower and an image capture rate of the light receiving part 2 is made lower. In other words, an exposure time is made longer. In this case, as shown in the graph that is corresponded to the condition (2) and the condition (4) of FIG. 6A, an average gray level of an image of the wafer W that is provided with a lower resistivity can be included in a defect detectable range. In other words, an image of the wafer W that is provided with a lower resistivity can be captured in an appropriate manner.

As shown in the case of a condition (6) for instance, a gain of the light receiving part 2 is maximized, an intensity of a light of the illuminating part 4 is maximized, and a moving speed of the inspection stage 3 is made lower. In this case, as shown in the graph that is corresponded to the condition (6) of FIG. 6A, an average gray level of an image of the wafer W that is provided with a lower resistivity can be included in a defect detectable range.

As described above, an average gray level of an image of the wafer W that is an inspection target can be adjusted by changing at least one of a gain of the light receiving part 2, an intensity of a light of the illuminating part 4, and a moving speed of the inspection stage 3 (and an image capture rate of the light receiving part 2). Consequently, an average gray level of an image can be set in a defect detectable range in an appropriate manner.

Figure 7:
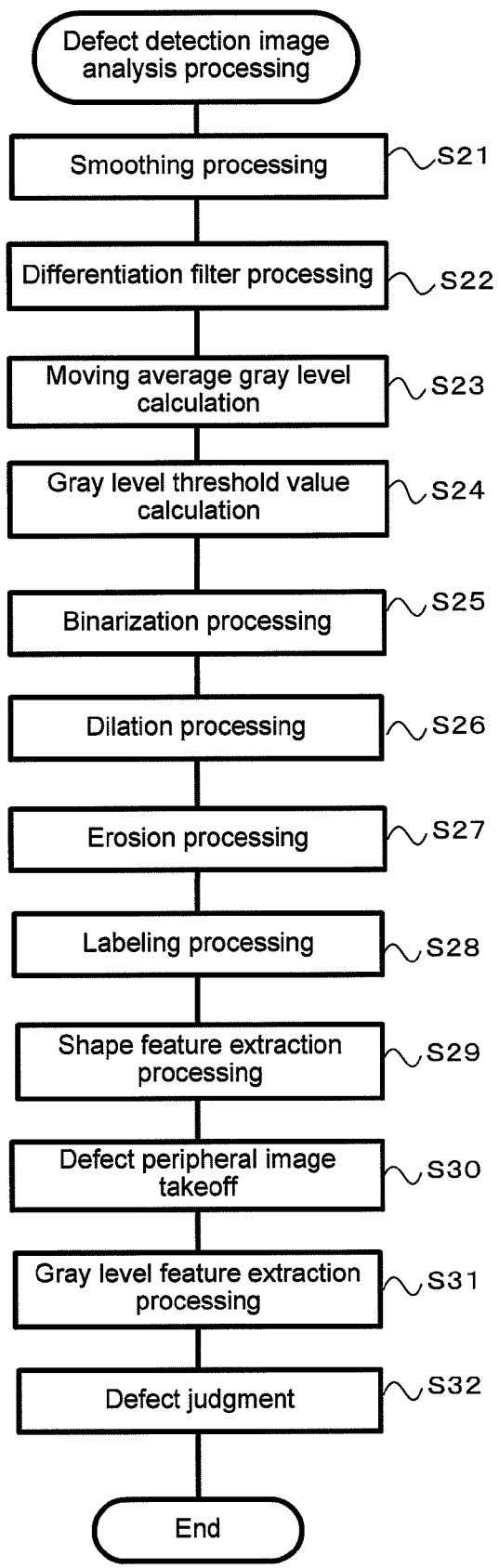
FIG. 7 is a flowchart of a defect detection image analysis processing in accordance with an embodiment of the present invention.

FIG. 7 is a flowchart of a defect detection image analysis processing in accordance with an embodiment of the present invention.

In the defect detection image analysis processing, the image processing part 6b executes a smoothing processing of each of the picture elements by using the image data of the wafer W (the original image data) that has been received from the control processing part 6a (step S21). In the smoothing processing, a gray level of the picture element that is a target is an average value of the gray level of n×n (for instance, 3×3) picture elements in which the target picture element is a center. In the present embodiment, the smoothing processing is executed for all picture elements of the image data, and the smoothing processing is executed multiple times. By this processing, the causes of error in the image data can be reduced.

In the next place, the image processing part 6b executes a predetermined differentiation filter processing for the image data (step S22). In the differentiation filter processing, a differentiation filter can be applied to the X direction (a direction perpendicular to the moving direction of the inspection stage 3: see FIG. 2) or can be applied to the Y direction (the moving direction of the inspection stage 3), and Laplacian can also be applied.

The image processing part 6b calculates a moving average gray level (a reference average gray level) of each of the picture elements by using the image data after the differentiation filter processing (step S23). In the present embodiment, a moving average gray level to each of the picture elements is obtained by averaging the gray level of picture elements of the predetermined number in the X direction somewhere around the picture element (for instance, 100 picture elements somewhere around the picture element). Moreover, a moving average gray level to each of the picture elements can also be obtained by averaging the gray level of picture elements of the predetermined number in the Y direction somewhere around the picture element (for instance, 100 picture elements somewhere around the picture element).

In the next place, the image processing part 6b calculates a gray level threshold value that is used for judging whether or not a picture element is a defect candidate picture element based on the moving average gray level of each of the picture elements (step S24). In the present embodiment, a value that is obtained by multiplying the moving average gray level of each of the picture elements by a predetermined coefficient (for instance, 0.3) is a gray level threshold value to each of the picture elements for instance. A fixed value can also be used as a gray level threshold value.

In the next place, the image processing part 6b executes a binarization processing for generating the binary image data (the binarization image data) that indicates whether or not a picture element is a defect candidate picture element by calculating a differential value (an absolute value of a difference) between a gray level of each of the picture elements of the image data and the moving average gray level of each of the picture elements and by comparing the differential value to each of the picture elements with the gray level threshold value that has been calculated to each of the picture elements (step S25). In the binarization processing, the data is converted to data that indicates that a picture element is a defect candidate picture element (for instance, 0: black) in the case in which a differential value for a picture element exceeds the gray level threshold value, and the data is converted to data that indicates that a picture element is not a defect candidate picture element (for instance, 1: white) in other cases.

In the next place, the image processing part 6b executes an dilation processing of a white color to the binarization image data that has been obtained in the step S25 (step S26). In the dilation processing, in the case in which there are more white picture elements in the range of n×n picture elements (n is a predetermined integer number) that includes the picture element for each of the picture elements for instance, the image processing part 6b executes a processing for making the picture element to be white. By the dilation processing, picture elements that is thought to be miscellaneous data in which one black picture element is included in white picture elements can be changed to white picture elements for instance. The dilation processing can be executed multiple times.

In the next place, the image processing part 6b executes a erosion processing of a white picture element (data provided with a value of "1") to the image data to which the dilation processing has been executed (step S27). In the erosion processing, in the case in which there are less white picture elements in the range of n×n picture elements (n is a predetermined integer number) that includes the picture element for each of the picture elements for instance, the image processing part 6b executes a processing for making the picture element to be black. By the erosion processing, a region of black that has been smaller by an influence of the dilation processing that has been executed in advance can be made larger, that is, made to be close to the original state. The erosion processing can be executed multiple times.

In the next place, in such a manner that defect candidate picture elements (black picture elements) that are connected to each other in the image data are handled as one gathering (a defect candidate region), the image processing part 6b executes a labeling processing for making a number correspond to the defect candidate region (step S28).

In the next place, the image processing part 6b executes a shape feature extraction processing for extracting a variety of shape parameters for each of the defect candidate regions to which a number has been corresponded (step S29). In the present embodiment, the image processing part 6b extracts an area S that is a total sum of the number of picture elements of the defect candidate region, a circumferential length l that is a length of a boundary line of the defect candidate region, a circularity e ($e=4\pi S/l^2$) of the defect candidate region, a gravity center position G of the defect candidate region, and the long and short ratio between a long straight line and a short straight line that pass through the gravity center position G.

In the next place, the image processing part 6b obtains the partial image data that includes the defect candidate region and the periphery thereof (for instance, a region that includes picture elements of a predetermined number in the vertical and horizontal directions of each of the picture elements) from the original image data (step S30).

In the next place, the image processing part 6b executes a gray level feature extraction processing for extracting a variety of gray level parameters for each of the defect candidate regions (step S31). In the present embodiment, the image processing part 6b decides the concave/convex of a gray level profile of the defect candidate region according to whether a profile of a gray level is plus or minus to the moving average gray level by using the partial image data, and obtains a ratio between the maximum difference of a gray level of the defect candidate region and the reference average gray level and the reference average gray level. Moreover, the image processing part 6b obtains the maximum gray level change rate (an absolute value of an inclination of a gray level profile) in the range that has been specified in advance for each of the boundary regions in the X and Y directions of a gray level profile that passes through the gravity center position G, and averages the gray level change rates at the four points that has been obtained. By this processing, an average gray level change rate $|a|_{ave}$ is calculated. The concave/convex of a gray level profile, the gray level ratio, and the average gray level change rate are also feature parameters that are related to the defect candidate region.

In the next place, the image processing part 6b judges whether the wafer W is acceptable or not as a product by using the feature parameters (a shape parameter and a gray level parameter) that have been calculated for each of the defect candidate regions and the defect judgment table 6c (step S32). More specifically, the image processing part 6b takes a first record from the defect judgment table 6c, and specifies a type of a defect according to whether or not the feature parameters for each of the defect candidate regions satisfy a defect classification condition that has been set for the record. Moreover, the image processing part 6b judges whether the wafer W is acceptable or not as a product according to whether or not an acceptance judgment condition of the record is satisfied. The image processing part 6b then takes all records of the defect judgment table 6c, and executes the above similar processing. By this processing, a type of a defect of the wafer W can be specified, and it can be judged whether the wafer is acceptable or not as a product in an appropriate manner.

Figure 8:
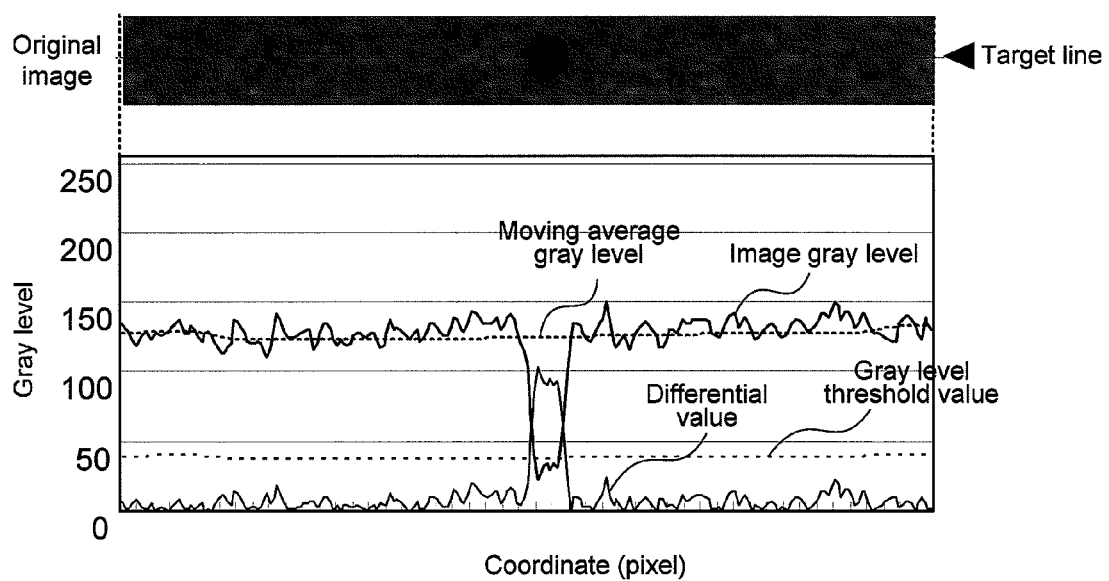
FIG. 8 is a view illustrating a binarization processing in accordance with an embodiment of the present invention.

FIG. 8 is a view illustrating a binarization processing in accordance with an embodiment of the present invention.

In the present embodiment, as shown in the step S25, the image processing part 6b executes the binarization processing by calculating a differential value between the moving average gray level of each of the picture elements and an image gray level and by comparing the differential value with the gray level threshold value. By using a differential value between a moving average gray level and an image gray level as described above, the non-uniformity of an image and the influence of a difference of a gray level for every wafer can be reduced. Consequently, a defect part can be detected in a more appropriate manner.

FIG. 9 is a view illustrating a binarization processing in accordance with an embodiment of the present invention.

Figure 9A:
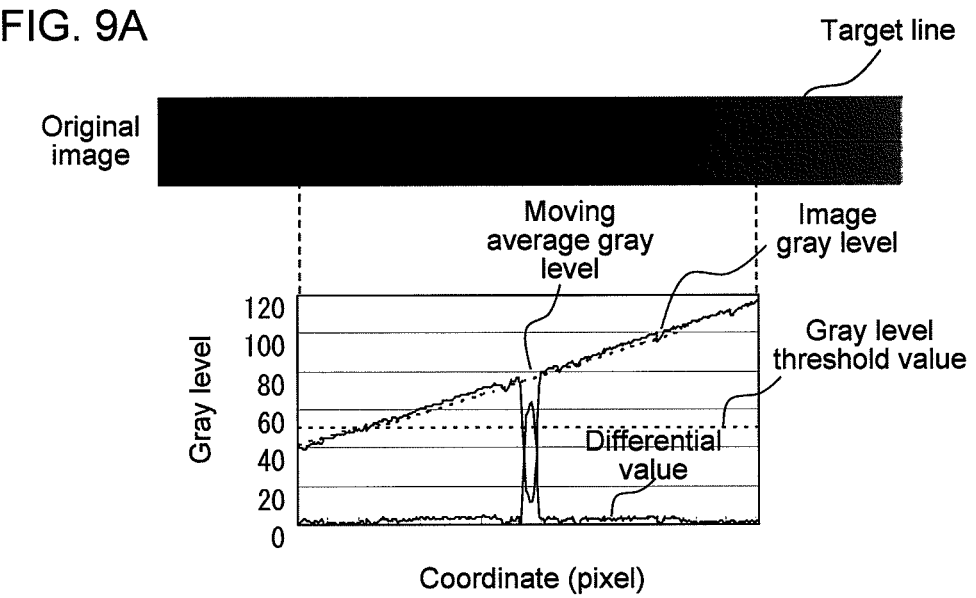
FIG. 9 is a view illustrating a binarization processing in accordance with an embodiment of the present invention.
Figure 9B:
Figure 9C:
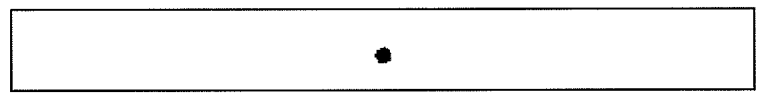

More specifically, FIG. 9A shows an image in which non-uniformity has occurred and the gray level profile thereof. FIGS. 9B and 9C show the results of the execution of the binarization processing in the state in which the non-uniformity of an image has occurred. In the case in which a threshold value is applied to an image gray level in the state in which the non-uniformity of an image has occurred as shown in FIG. 9B, an image non-uniformity region other than a defect part is also a target of the binarization processing. However, a defect part can be detected in an appropriate manner without an influence of the non-uniformity of an image by applying a threshold value to a differential value as shown in FIG. 9C.

FIG. 10 is a view illustrating a binarization processing in which a gray level threshold value has been modified in accordance with an embodiment of the present invention.

Figure 10A:
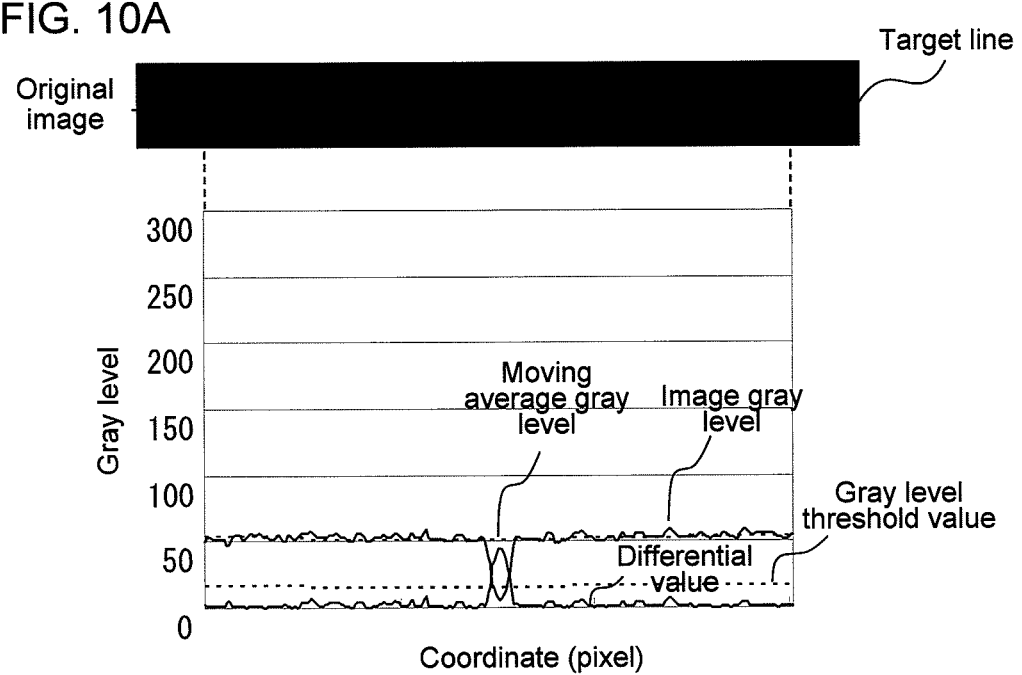
FIG. 10 is a view illustrating a binarization processing in which a gray level threshold value has been modified in accordance with an embodiment of the present invention.
Figure 10B:
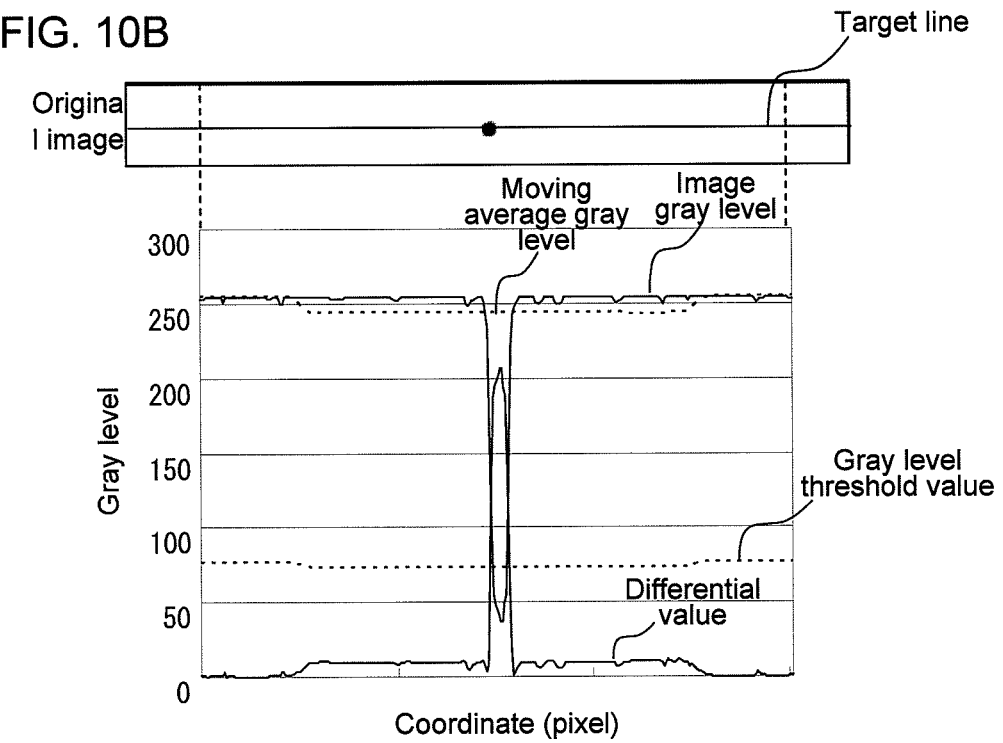

More specifically, FIG. 10 shows the result of a detection of a defect after obtaining images that are provided with different average gray level for a defect of 100 μm that exists in the face of the wafer W. FIG. 10A shows the result of a detection of a defect for an image that is provided with a low gray level. FIG. 10B shows the result of a detection of a defect for an image that is provided with a high gray level.

As shown in FIGS. 10A and 10B, a defect that exists in the wafer W can be detected in an appropriate manner by modifying a gray level threshold value according to a grayscale level of an image. In the present embodiment, a gray level threshold value is decided by multiplying the moving average gray level by a predetermined coefficient, and the higher the moving average gray level is, the higher the gray level threshold value is. Consequently, a defect of the wafer W can be detected in a more appropriate manner While the preferred embodiments in accordance with the present invention have been described above, the embodiments are examples for describing the present invention and the scope of the present invention is not restricted to the embodiments. It is obvious that various changes, modifications, and functional additions can be thus made without departing from the scope of the present invention.

The first and second modification examples that are modification examples in accordance with the present invention will be described in the following.

Figure 11:
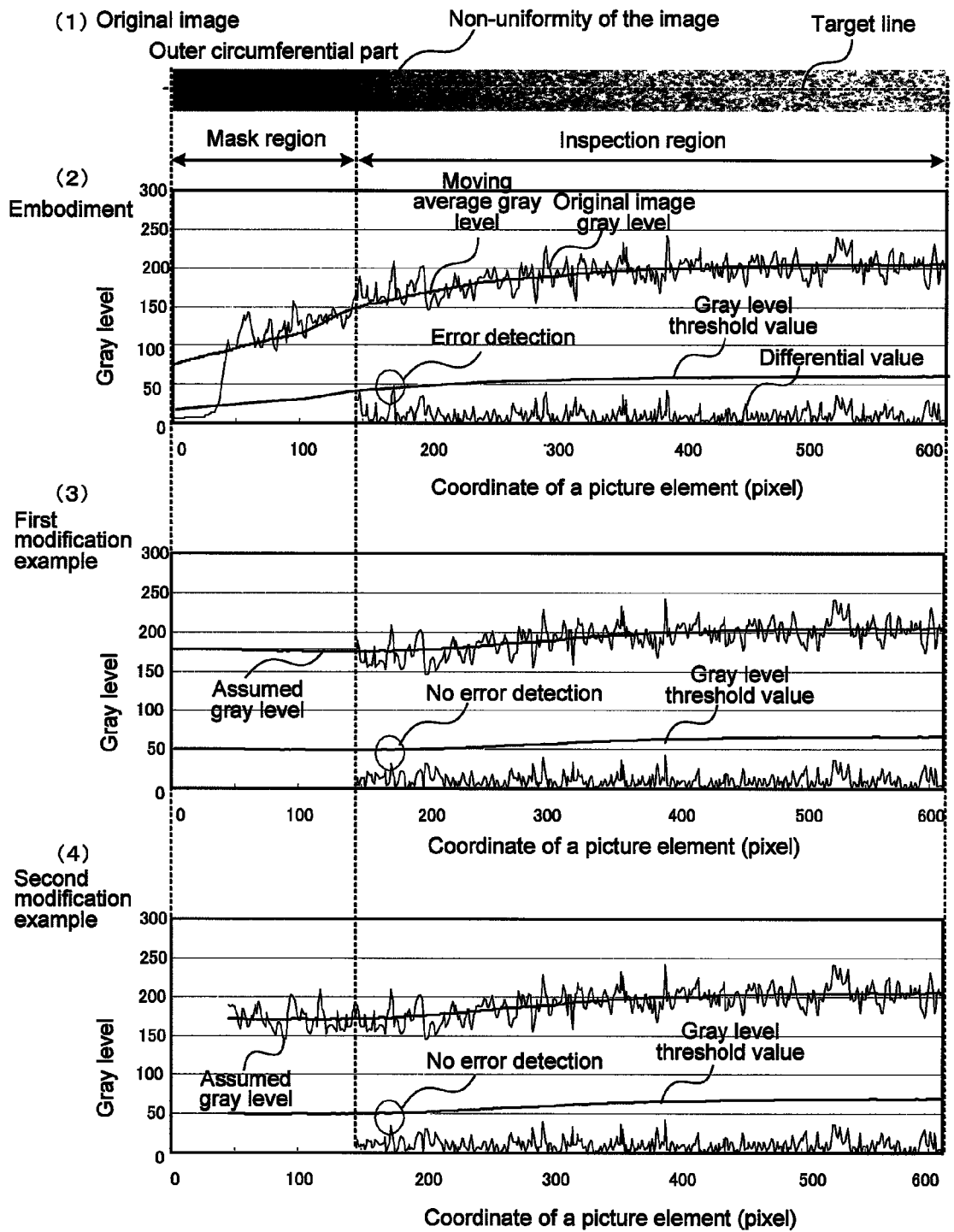
FIG. 11 is a view illustrating a calculation method of a moving average gray level in accordance with a modification example of the present invention.

FIG. 11 is a view illustrating a calculation method of a moving average gray level in accordance with a modification example of the present invention.

For the wafer defect inspection apparatus 1 in accordance with the above embodiment, there are less intensity of a transmitted light at the periphery of the wafer W due to an influence of the non-uniformity of an illumination and a sagging of the periphery of the wafer. Consequently, as shown in FIG. 11(1), a region around the periphery of the wafer W is set as a region that is not an inspection target (a mask region).

In the above embodiment, as shown in FIG. 11(2), a moving average gray level to each of the picture elements is obtained by averaging the gray level of 100 picture elements somewhere around the picture element in the predetermined direction (for instance, in the X direction). Consequently, for the picture element of the inspection region close to the mask region of the wafer W, a moving average gray level becomes lower due to an influence of a gray level of the picture element in the mask region, and there is a possibility that the error detection is carried out as a defect candidate picture element. In the case in which there is the non-uniformity of an image in the inspection region close to the mask region as shown in FIG. 11(1) for instance, a differential value between a gray level of the non-uniformity part of the image and the moving average gray level of the part exceeds the threshold value as shown in FIG. 11(2). Therefore, the error detection of the picture element of the non-uniformity part of the image may be carried out as a defect candidate picture element in some cases.

On the other hand, for a first modification example, a moving average gray level of each of the picture elements is calculated while supposing that a gray level of a picture element in the mask region is equivalent to a gray level of a picture element at a boundary part between the mask region and the inspection region. By this configuration, even in the case in which there is the non-uniformity of an image as shown in FIG. 11(1), a differential value between a gray level of the non-uniformity part of the image and the moving average gray level of the part does not exceed the threshold value as shown in FIG. 11(3). Therefore, the error detection of the picture element of the non-uniformity part of the image is not carried out as a defect candidate picture element.

Moreover, for a second modification example, a moving average gray level of each of the picture elements is calculated while supposing that a gray level of a picture element in the mask region is equivalent to a gray level of a picture element at a symmetric position to a boundary part between the mask region and the inspection region. By this configuration, even in the case in which there is the non-uniformity of an image as shown in FIG. 11(1), a differential value between a gray level of the non-uniformity part of the image and the moving average gray level of the part does not exceed the threshold value as shown in FIG. 11(4). Therefore, the error detection of the picture element of the non-uniformity part of the image is not carried out as a defect candidate picture element. As a result, the error detection of a defect can be reduced.

The present invention can also be configured as described in the following. In above embodiment for instance, the entire image of the wafer W is obtained by moving the inspection stage 3. However, the entire image of the wafer W can also be obtained by moving the light receiving part 2, the illuminating part 4, and the light guide 5 without moving the inspection stage 3 for instance. The point is that the entire image of the wafer W is obtained by moving the inspection stage 3, the light receiving part 2, the illuminating part 4, and the light guide 5 in a relative manner.

In above embodiment moreover, an average gray level of an image of the wafer W is used as a gray level that is a reference of an image of the wafer. However, the present invention is not restricted to this configuration, and the darkest gray level of an image of the wafer W can also be used for instance. Moreover, an average gray level of an inspection region of the wafer W can also be used.

In above embodiment moreover, an irradiation condition of the illuminating part 4 is modified, a photodetective condition of the light receiving part 2 is then modified in the case in which the irradiation condition cannot be modified, and an exposure condition is then modified in the case in which the photodetective condition cannot be modified. However, the present invention is not restricted to this configuration, and a sequence of a modification of the irradiation condition, the photodetective condition, and the exposure condition can also be changed to a different sequence. Moreover, a plurality of conditions of the irradiation condition, the photodetective condition, and the exposure condition can also be modified at one time. Furthermore, a plurality of sets of the irradiation condition, the photodetective condition, and the exposure condition is prepared for instance, and a modification target that is used can also be selected from the sets.

In above embodiment moreover, a moving average gray level is calculated by using the image data in which a smoothing processing and a differentiation filter processing are executed to the original image data. However, a moving average gray level can also be calculated by using the original image data without executing the smoothing processing and the differentiation filter processing.

REFERENCE SIGNS LIST

1: Wafer defect inspection apparatus
2: Light receiving part

3: Inspection stage
4: Illuminating part
5: Light guide
6: Processing apparatus
6a: Control processing part
6b: Image processing part
6c: Defect judgment table
W: Wafer

The invention claimed is:

1. A wafer defect inspection apparatus, comprising:
   a wafer mount configured to mount a wafer that is an inspection target;
   an irradiator configured to irradiate the wafer with an infrared light;
   an imager configured to image the wafer that has been irradiated with the infrared light;
   a reference moving average gray level calculator configured to calculate a gray level that has been obtained by averaging gray levels of a plurality of picture elements in the a predetermined range including an inspection target picture element in a plurality of picture elements that are arranged in the a predetermined line direction as a reference moving average gray level of the inspection target picture element for each of the inspection target picture elements in a region that is an inspection target of the wafer in an image of the wafer that has been imaged by the imager;
   a differential value calculator configured to calculate a differential value between the reference moving average gray level of the inspection target picture element and a gray level of the inspection target picture element for each of the inspection target picture elements;
   a defect candidate picture element judger configured to judge whether each of the inspection target picture elements is a defect candidate picture element by comparing the differential value for each of the inspection target picture elements with the a predetermined threshold value; and
   an inspector configured to inspect a defect of the wafer based on the defect candidate picture element.

2. The wafer defect inspection apparatus according to claim 1, wherein the reference moving average gray level calculator is configured to calculate the reference moving average gray level, where a gray level of a picture element, in a region that is exempt from the inspection, is a boundary with the region that is an inspection target, when a picture element in the predetermined range in the predetermined line direction corresponds to the picture element in the region that is exempt from the inspection around the outer circumference of the wafer.

3. The wafer defect inspection apparatus according to claim 1, wherein the reference moving average gray level calculator is configured to calculate the reference moving average gray level, where a gray level of a picture element, in a region that is exempt from the inspection, is at a symmetric position to a boundary with the region that is an inspection target on the straight line in the predetermined line direction, when a picture element in the predetermined range in the predetermined line direction corresponds to the picture element in the region that is exempt from the inspection around the outer circumference of the wafer.

4. The wafer defect inspection apparatus according to claim 1, wherein the inspector comprises:
   a defect candidate region specifier configured to specify a defect candidate region based on the defect candidate picture element; and
   a defect type judger configured to judge whether a defect candidate region is corresponded to the predetermined defect type based on at least one of the concave/convex of a gray level profile of the defect candidate region, a gray level ratio that is a ratio between the maximum difference of a gray level and a reference moving average gray level for the defect candidate region and a reference moving average gray level, an average gray level change rate of the defect candidate region, an area of the defect candidate region, a circularity of the defect candidate region, and a ratio between a long width and a short width when a center of gravity of the defect candidate region is a reference.

5. The wafer defect inspection apparatus according to claim 1, wherein the inspector further comprises an acceptance judger configured to judge whether the wafer is acceptable as a product based on the number of defect candidate regions that are corresponded to the predetermined defect type.

6. The wafer defect inspection apparatus according to claim 1, further comprising a threshold value decider configured to decide the predetermined threshold value to each of the inspection target picture elements based on the reference moving average gray level of each of the inspection target picture elements.

7. The wafer defect inspection apparatus according to claim 6, wherein the threshold value decider is configured to decide a value that is obtained by multiplying the reference moving average gray level by the predetermined value as the predetermined threshold value.

8. A method for inspecting a wafer defect based on an image of a wafer that is an inspection target, comprising:
   calculating a gray level that has been obtained by averaging gray levels of a plurality of picture elements in the a predetermined range including an inspection target picture element in a plurality of picture elements that are arranged in the a predetermined line direction as a reference moving average gray level of the inspection target picture element for each of the inspection target picture elements in a range that is an inspection target of the wafer in the image;
   calculating a differential value between the reference moving average gray level of the inspection target picture element and a gray level of the inspection target picture element for each of the inspection target picture elements;
   judging whether each of the inspection target picture elements is a defect candidate picture element by comparing the differential value for each of the inspection target picture elements with the a predetermined threshold value; and
   inspecting a defect of the wafer based on the defect candidate picture element.

* * * * *